(12) United States Patent
Taylor

(10) Patent No.: US 7,066,889 B2
(45) Date of Patent: *Jun. 27, 2006

(54) SCANNING PROBE

(75) Inventor: James D. Taylor, St. Louis, MO (US)

(73) Assignee: Envisioneering, LLC, St. Louis, MO (US)

(*) Notice: Subject to any disclaimer, the term of this patent is extended or adjusted under 35 U.S.C. 154(b) by 136 days.

This patent is subject to a terminal disclaimer.

(21) Appl. No.: 10/806,254

(22) Filed: Mar. 22, 2004

(65) Prior Publication Data

US 2004/0204650 A1    Oct. 14, 2004

Related U.S. Application Data

(63) Continuation-in-part of application No. 10/271,897, filed on Oct. 16, 2002, now Pat. No. 6,709,397.

(60) Provisional application No. 60/329,464, filed on Oct. 16, 2001.

(51) Int. Cl.
*A61B 8/14* (2006.01)

(52) U.S. Cl. .................................................. 600/459

(58) Field of Classification Search ................ 600/424, 600/437–472; 607/122
See application file for complete search history.

(56) References Cited

U.S. PATENT DOCUMENTS

| | | |
|---|---|---|
| 4,374,525 A | 2/1983 | Baba |
| 4,757,818 A | 7/1988 | Angelsen |
| 4,802,458 A | 2/1989 | Finsterwald et al. |
| 4,819,650 A | 4/1989 | Goldstein |
| 4,841,979 A | 6/1989 | Dow et al. |
| 5,048,529 A | 9/1991 | Blumenthal |
| 5,050,610 A | 9/1991 | Oaks et al. |
| 5,054,491 A | 10/1991 | Saito et al. |
| 5,070,879 A | 12/1991 | Herres |
| 5,090,414 A | 2/1992 | Takano |
| 5,105,819 A | 4/1992 | Wollschlager et al. |
| 5,152,294 A | 10/1992 | Mochizuki et al. |
| 5,159,931 A | 11/1992 | Pini |
| 5,170,793 A | 12/1992 | Takano et al. |
| 5,181,514 A | 1/1993 | Solomon et al. |
| 5,361,768 A | 11/1994 | Webler et al. |
| 5,394,878 A | 3/1995 | Frazin et al. |
| 5,460,179 A | 10/1995 | Okunuki et al. |
| 5,474,072 A | 12/1995 | Shmulewitz |
| 5,592,942 A | 1/1997 | Webler et al. |
| 5,611,343 A | 3/1997 | Wilson |
| 5,769,079 A | 6/1998 | Hossack |
| 5,842,473 A | 12/1998 | Fenster et al. |
| 5,875,778 A | 3/1999 | Vroegop |

(Continued)

*Primary Examiner*—Ali Imam
(74) *Attorney, Agent, or Firm*—Paul M. Denk

(57) ABSTRACT

An ultrasound cavital probe suitable for transrectal or other usage, includes an ultrasound probe, having an outer housing, a pair of motors within one end of the housing, a first shaft operatively associated with one of the motors to provide longitudinal movement to the ultrasound transducer, while a second shaft operatively associated with the second motor, and which extends through the hollow interior of the first said shaft, provides for pivotal or rotary movement to the ultrasound transducer and probe, to furnish a 2-dimensional view of the surrounding anatomy, and which in combination with the movement from the first shaft, furnishes a 3-dimensional volumetric scan of the surrounding anatomy, along with facilitating the image plane movements normally obtained by a standard probe while used in a stepping device.

3 Claims, 11 Drawing Sheets

U.S. PATENT DOCUMENTS

| | | |
|---|---|---|
| 5,931,788 A | 8/1999 | Keen et al. |
| 5,964,707 A | 10/1999 | Fenster et al. |
| 6,004,271 A | 12/1999 | Moore |
| 6,200,269 B1 | 3/2001 | Lin et al. |
| 6,245,020 B1 * | 6/2001 | Moore et al. ............... 600/466 |
| 6,709,397 B1 * | 3/2004 | Taylor ........................ 600/459 |

* cited by examiner

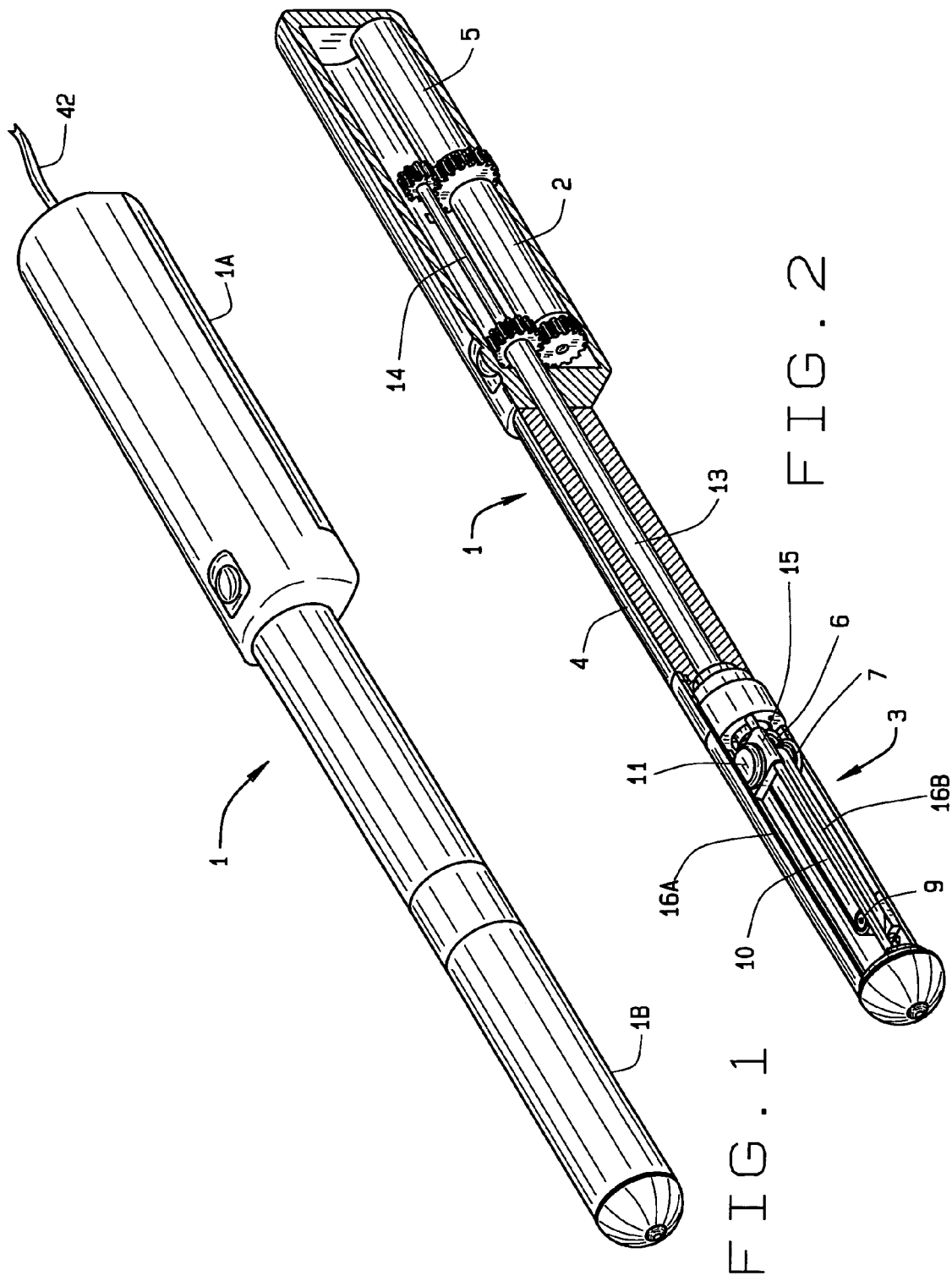

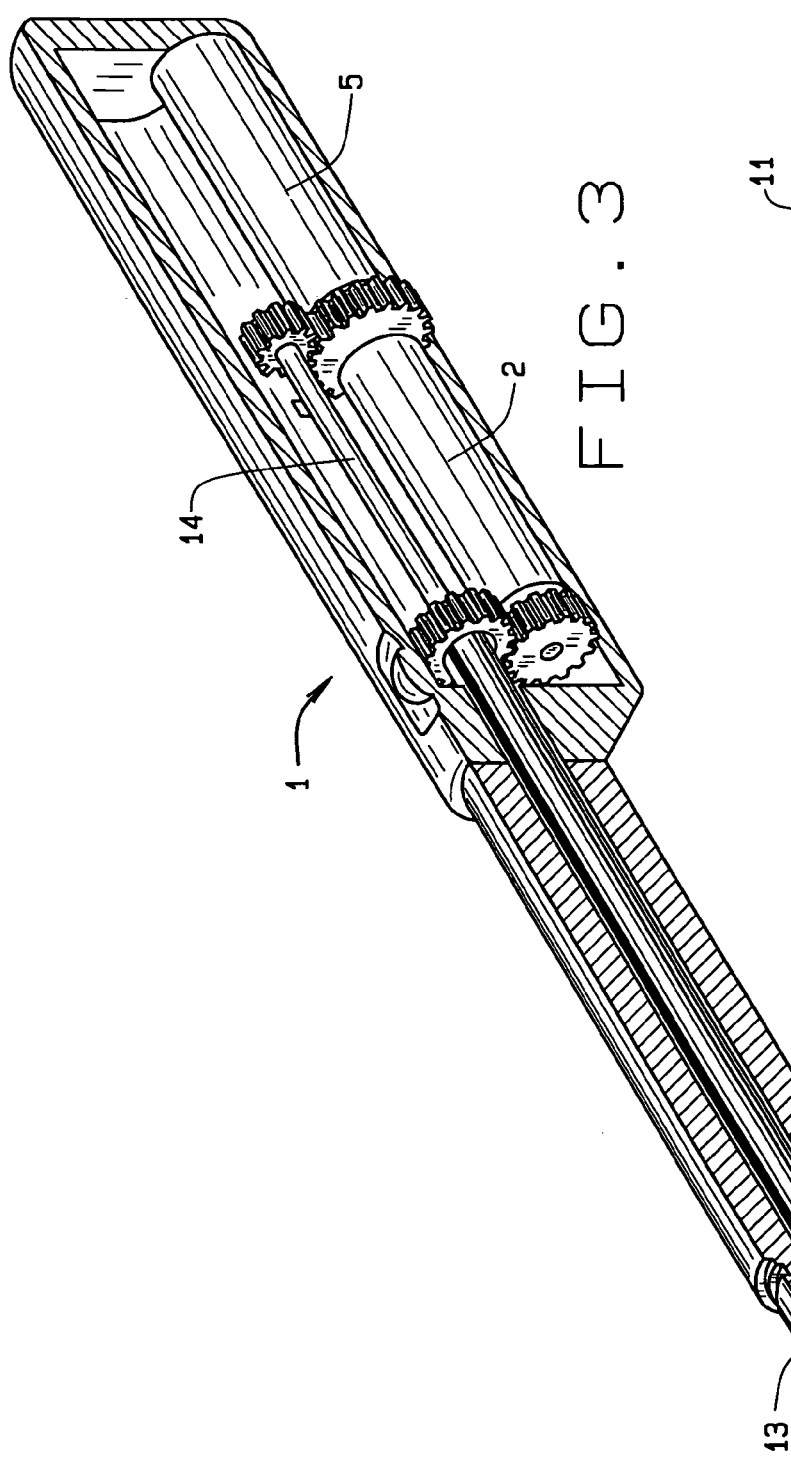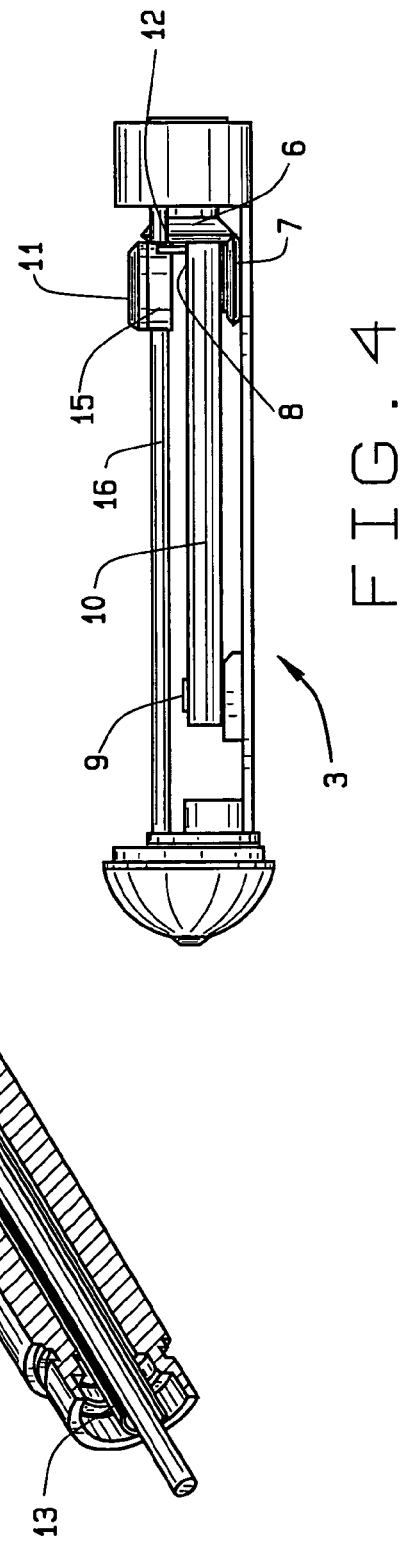

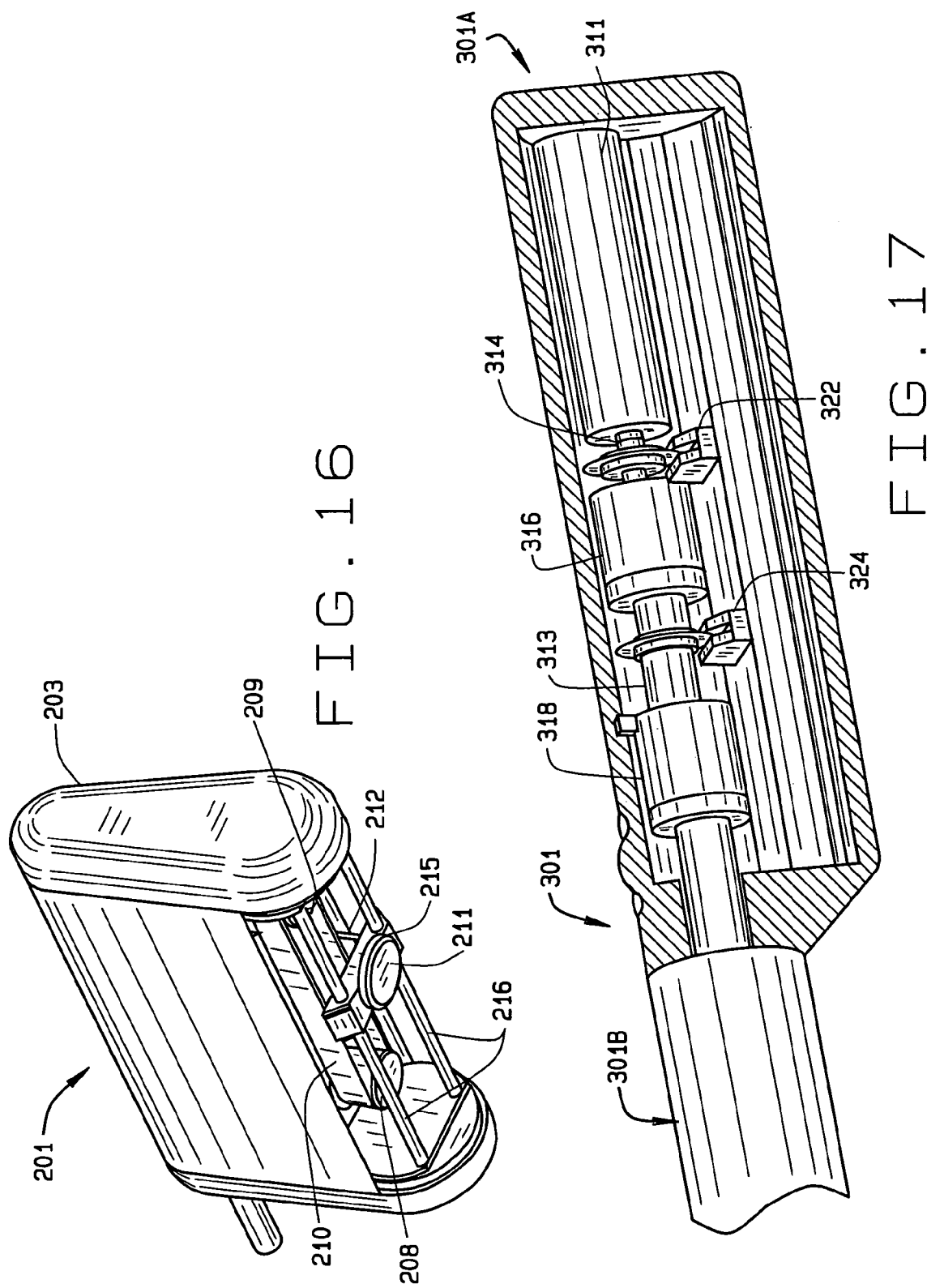

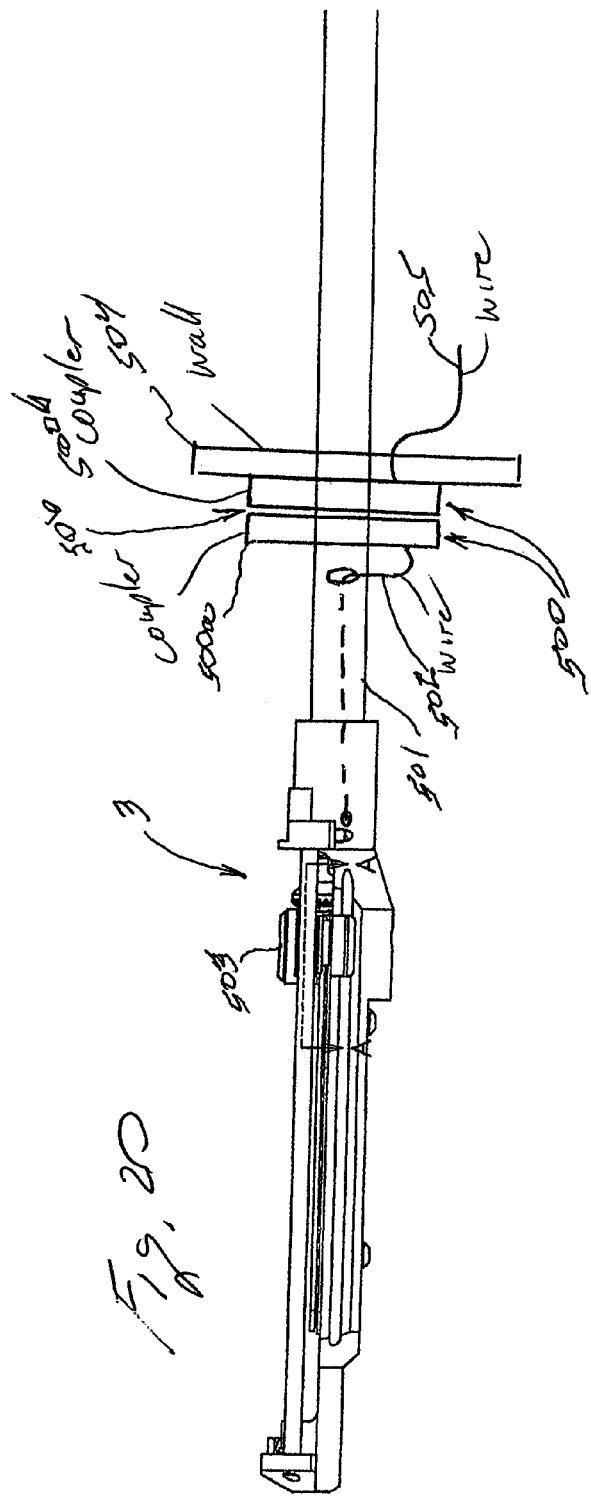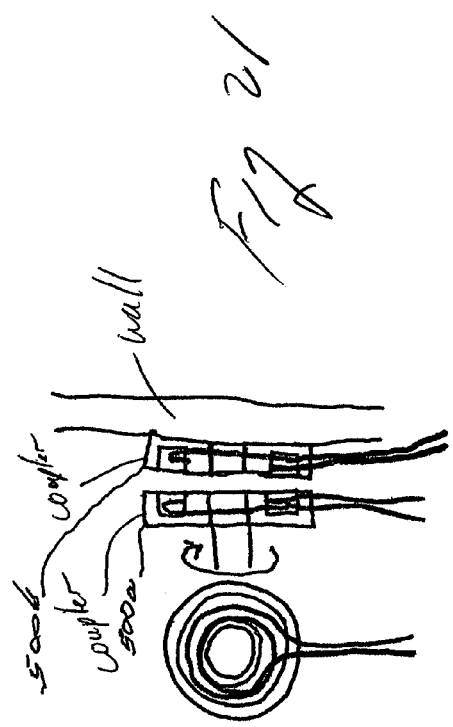

SCANNING PROBE

CROSS-REFERENCE TO RELATED APPLICATIONS

This continuation-in-part patent application claims priority to provisional application Ser. No. 60/329,464 filed Oct. 16, 2001, which claims priority to the non provisional patent application having Ser. No. 10/271,897, which was filed on Oct. 16, 2002, and which is now U.S. Pat. No. 6,709,397.

BACKGROUND OF THE INVENTION

This invention relates to ultrasonic medical imaging systems, and more particularly pertains to probes and scanning devices used in combination and in conjunction with ultrasonic medical imaging equipment, to provide a better focusing upon the potential site of disease at particular locations in the body, and more specifically the prostate, and in addition, provides a means for guiding the insertion and implantation of the biopsy needle or other treatment devices into a precise location, during medical treatment.

Ultrasound has become an important diagnostic tool for the medical professionals. Generally, ultrasound scanning means can be categorized as either a "cavital" imaging device, or a "body" imaging device. The cavital imaging devices, often referred to as "probes", are usually of the type that are inserted into a cavity of the patient to image organs therein or those arranged juxtapose or adjacent to the cavity, to provide for a precise picture of the surrounding area. Cavital probes are often specifically designed for the configuration of the cavity to be imaged. Cavital probes include the type that provide transrectal imagining, such as for use for the detection of prostate cancer, and rectal cancer, in addition to transvaginal probes. In addition, transesophagual probes also provide for imaging.

Ultrasound works by using a transducer to generate a narrow pulse of sound, which travels through the surrounding tissue. The pulse of sound is then reflected back to and captured by the transducer, with the density and distance of tissue affecting how the signal is reflected. Currently two main types of transrectal cavital probes are in use: a bi-plane mechanical probe and a bi-plane solid-state probe. The standard mechanical probe contains one or more transducers that are mounted inside the hollow casing at the tip of the probe. The transducer(s) either pivot or rotate quickly within the tip (approximately five to ten times per second) to generate and receive pulses at multiple points. Depending upon the movement used, a pie-shaped cross sectional image generated either inline with the probe tip (longitudinally) or perpendicular thereto (transversely). This dual axes image capability is referred to as bi-plane imagining. The solid-state probe operates in a similar manner, except that the single transducer is replaced with inline columns of very small transducers. The transverse columns are wrapped around a small portion of the diameter of the probe and longitudinal columns runs approximately sixty millimeters along the length of the probe. Instead of pivoting a transducer, the multiple transducers of each column are sequentially pulsed to create a cross sectional image. Therefore, like the mechanical probe, the solid-state probe is able to generate dual axis, bi-plane images.

Ultrasound has become the primary method of imaging the prostate and is an integral component in a number of widely used prostate cancer treatment procedures. A rectally inserted ultrasound probe of either type, in conjunction with imaging software, allows the doctor to display a two dimensional image of the prostate on the longitudinal plane, and a two dimensional image on the transverse plane. The doctor can view these images to evaluate the prostate for cancer, and if necessary prescribe a treatment regimen. Both types of current probes must be mounted on a large stand, referred to as a "stepper and stabilizer". The stepper and stabilizer is used to maintain the stability of the probe within the rectum and also allow it to be precisely moved in and out and to be rotated by the use of hand operated controls. The in and out movement is typically performed in five millimeter increments to facilitate the collection of eight to ten 2D transverse images that a computer then assembles to create a rough 3-dimensional approximation of the 3D volume of the prostate. The "free hand"/diagnostic rotational movement is used to view the prostate, needles and other treatment devices in the longitudinal mode. Conventional probes, in combination with the steppers, have multiple operational problems and limitations.

Further, a very popular treatment for prostate cancer is brachytherapy, in which a series of tiny radioactive seeds are embedded in the prostate in an attempt to destroy any present carcinoma. A rectally inserted ultrasound probe is used to guide the insertion of needles through the skin and into the prostate as part of this treatment. Regardless of the treatment option utilized, a transrectal ultrasound probe is needed to help diagnose, plan, and most often guide, the treatment procedure.

Existing probe designs suffer from a number of problems and deficiencies. Moving the probe in and out of the rectum or vagina can be extremely uncomfortable for the patient, and it also causes the prostate, needles, and radioactive seeds and other diagnostic and treatment devices to move, therefore constantly changing their position during diagnostic and the treatment methods. All of the probe movement is hand-initiated and powered by the physician. As a result, the process of taking the multiple images is extremely slow, increasing the length of the time the probe must be in the patient's rectum and further increasing the time the doctor spends on the procedure. Also, the readings and scans may be inaccurate due to the manually recorded location. Also standard steppers usual only move in large, five millimeter increments more or less, limiting the number of cross sections obtained and limiting the information available to the physician after the probe is removed from the patient. Further, because of the need to move the whole probe, the stepper must be very steady. Consequently, steppers are very large and expensive devices, substantially increasing the cost of an ultrasound treatment system. As such, the use of transrectal imaging has been limited and has not fully reached its potential as a preferred diagnostic tool.

Various prior art imaging systems have been available in the art, as can be seen from a number of publications. For example, the patent to Fenster, et al, U.S. Pat. No. 5,964,707, shows a 3-dimensional imaging system. While this particular 3-dimensional ultrasound imaging system may provide for an inputting of ultrasound signals from a transducer, it essentially utilizes the ultrasound probe to provide for linear scanning, wherein successive 2-dimensional images of the target volume are detected, and then digitized, to obtain other images. Another patent to Fenster, U.S. Pat. No. 5,842,473, also upon a 3-dimensional imaging system, operates on the same principle.

The patent to Wilson, U.S. Pat. No. 5,611,343, discloses a high resolution 3-dimensional ultrasound imaging system. It provides ultrasound imaging for generating high resolution, 3-dimensional images of the body for medical imaging purposes. The system includes a housing and a rotatable disc, at one end of its probe, to obtain its ultrasound images.

The patent to Herries, U.S. Pat. No. 5,070,879, shows another ultrasound imaging method and apparatus.

The patent to Frazien, U.S. Pat. No. 5,394,878, discloses a method for 2-dimensional real time color Doppler ultrasound imaging of bodily structures through the gastrointestinal wall.

The United States patent to Wollschlager, et al, U.S. Pat. No. 5,105,819, shows an ultrasound endoscope device.

The patent to Saito, et al, U.S. Pat. No. 5,054,491, shows another ultrasonic endoscope apparatus.

The United States patent to Keen, et al, U.S. Pat. No. 5,931,788, discloses the method and apparatus for imaging internal organs and vascular structures through the gastrointestinal wall.

The patent to Hossack, U.S. Pat. No. 5,769,079, discloses the method and apparatus for determining quantitative measures of flow parameters.

The United States patent to Oaks, et al, U.S. Pat. No. 5,050,610, explains the transesophageal ultrasonic scan head.

The United States patent to Angelsen, U.S. Pat. No. 4,757,818, shows an ultrasonic transducer probe with linear motion drive mechanism. This particular patent appears to be more related to the specific type of motor means that are used to drive its probe in a linear motion.

The patent to Goldstein, U.S. Pat. No. 4,819,650, shows an ultrasound assembly comprised of a dual transducer probe, and a hollow casing. The casing acts as a guide to allow the probe to be maintained in one of two positions, so as to facilitate the positional registration of two separate transducers or arrays of transducers. Goldstein does not disclose a means for longitudinally positioning a transducer within the body of a probe, nor does it facilitate the image plane movements normally obtained by a standard probe when used in a stepping device.

The patent to Dow, et al, U.S. Pat. No. 4,841,979, shows an ultrasonic probe with a single transducer. The transducer is mounted on a pivoting platform which can also be rotated. This patent does not disclose a means of longitudinally positioning a transducer within the body of a probe, nor does it facilitate the image plane movements normally obtained by a standard probe when used in a stepping device.

The patent to Blumenthal, U.S. Pat. No. 5,048,529, shows an ultrasonic probe with a single transducer. The transducer is mounted on a pivoting platform. A pulley arrangement and flexible belt are used to cause the transducer platform to pivot so as to be able to vary the pivot arc distance. This patent does not disclose a means of longitudinally positioning a transducer within the body of a probe, nor does it facilitate the image plane movements normally obtained by a standard probe when used in a stepping device.

The patent to Bradley, U.S. Pat. No. 5,070,879, shows an ultrasound imaging apparatus using a longitudinal array of multiple transducers. The phased array is oscillated along the axis of the probe to generate transverse images. This patent does not disclose a means of longitudinally positioning a transducer within the body of a probe, nor does it facilitate the image plane movements normally obtained by a standard probe when used in a stepping device.

The patent to Takano, U.S. Pat. No. 5,090,414, shows an intercavity ultrasound probe. This is a probe of the mechanical scan type. As noted, this device includes a transducer element that locates at a distal end of the body, it includes a stab needle guide for guiding a stab needle and means for transmitting a torque from the driving source to the rotating shaft.

The patent to Pini, No. U.S. Pat. No. 5,159,931, shows an intra-cavity probe with a single transducer. The transducer is maintained on a platform which can be rotated containing a transducer which can be pivoted. This patent does not disclose a means of longitudinally positioning a transducer within the body of a probe, nor does it facilitate the image plane movements normally obtained by a standard probe when used in a stepping device.

Another patent to Takano, U.S. Pat. No. 5,170,793, shows an ultrasonic probe assembly with a single transducer for use in blood vessels. This patent shows mean for rotating the transducer within the tip of the probe, even if the probe body has been bent. This patent, though, does not disclose a means for providing longitudinal positioning of a transducer within the body of the probe, nor does it facilitate the image plane movements normally obtained by a standard probe when used in a stepping device.

The patent to Solomon, et al, U.S. Pat. No. 5,181,514, shows an ultrasonic probe for use in the esophagus. This device contains a motor which can rotationally turn an array of transducers to generate moveable scan planes. This device also shows means for positioning of the probe to provide feedback on the location of the probe. But, the patent does not disclose a means of longitudinally positioning a transducer within the body of a probe, nor does it facilitate the image plane movements normally obtained by a standard probe when used in a stepping device.

The patent to Webler, et al, U.S. Pat. No. 5,361,768, shows a longitudinal positioning translator for use with an ultrasound probe. The positioning translator physically moves the ultrasound probe within a body vessel. This patent does not disclose a means for longitudinally positioning a transducer within the probe body.

The patent to Okunuki, et al, U.S. Pat. No. 5,460,179, shows an ultrasound body scanner utilizing an array of transducers. The transducers are arranged linearly on a transducer unit within the hollow casing of the scanner. The transducer unit may be pivoted within the hollow body of the scanner, such that the image plane of the transducers is swung back and forth.

The patent to Schmulewitz, U.S. Pat. No. 5,474,072, shows methods and apparatus for performing sonomammography. The apparatus of this device combines ultrasonic scanning, affixed to a moveable carriage, and also mammography imaging means.

Another patent to Webler, U.S. Pat. No. 5,592,942, shows an automated longitudinal position translator for ultrasonic imaging probes, and methods of using the same. The positioning translator physically moves the ultrasonic probe within a blood vessel.

The patent to Moore, U.S. Pat. No. 6,004,271, discloses a combined motor drive and automated longitudinal position translator for ultrasonic imaging system. This discloses a vascular ultrasound imaging system with automated longitudinal position translator. A catheter containing the ultrasonic scanner is inserted into the vein within a catheter. Once a catheter is correctly positioned within a vein, the ultrasound scanner may be drawn back out of the catheter to affect a scanning of a portion of the vein.

Finally, the patent to Lin, et al, U.S. Pat. No. 6,200,269, shows a forward scanning ultrasound catheter probe. The transducer is maintained on a platform at the distal end of the probe, the platform being pivoted via a piezoelectric drive to create a scanning plane.

BRIEF SUMMARY OF THE INVENTION

This invention relates primarily to scanning technology, and more particularly pertains to an ultrasonic medical imaging system that provides for the detection and location of disease, such as cancer, furnishes means for providing a full image of the scanned areas, and for precise locating of medical instrumentation used in the treatment and detection of such disease.

Generally, the instrument of this invention, comprising basically a scanning probe, and the supporting instrumentation that is used in conjunction therewith, provides a scanning probe, normally one that will sit upon a stand, within a cradle, but principally provides support for the probe of this invention. The purpose of the probe is to emit ultrasonic pulses, so that an accurate image of tissue or the prostate, when that is what is being observed, to obtain a thorough detection where a carcinoma may be located. The probe of this device, which emits the ultrasonic pulses, incorporates a motor or motors, rearwardly of the ultrasonic probe, so that the means that emits the ultrasonic pulse can not only be rotated, or pivoted, to any degree, even up to 360 degrees, to provide a 2-dimensional image at the precise plane of the ultrasound, but likewise, the probe can be longitudinally reciprocated, in order to furnish the actual, not computer interpolated, 3-dimensional image, required and desired, to provide for the precise detecting and treatment of the diseased organ. A first motor or other means provides for the pivotal or revolutionary motion to the ultrasound emitter, while the second motor or other means furnishes its longitudinal displacement, as required for actual 3-dimensional imaging.

A first motor means turns an initial or outer shaft, while the second motor means turns an inner shaft, concentrically located within the outer shaft. The turning of an inner shaft provides for rotating of a belt or belts, while the turning of the outer shaft provides for a rotation of the probe carriage assembly, so that a complete 360° image may be obtained, when the probe is inserted, as for example, within a rectum, to obtain an accurate image of the prostate, during detection, and also while treatment is being performed.

A belt means included within the probe, and which is subject to movement of the inner shaft, shifts the ultrasound unit longitudinally, while the belt means, and all of its associated operating mechanisms, are revolved to provide for the 360° scan by the ultrasound. The ultrasound transducer is associated with the mechanism, and it is shifted by means of the motor, belts, and other components during their functionality, to provide for these identified movements, along the various axes, to furnish the ultrasound scanning of the surrounding anatomy, and to achieve an accurate picture of the organ being observed or treated.

Accordingly, an object of the present invention is to provide a cavital or body scanning probe of mechanical design which facilitates the use of the ultrasound in a range of diagnostic and treatment uses. An advantage of the present invention is the structure of a device which allows the transducer or transducers to move reciprocally, in and out longitudinally, within the hollow cavity of the scanning means, while at the same time obtaining its simultaneously rotating or pivoting, allowing the transverse or longitudinal images to also move in and out, and rotate, thereby allowing multiple transverse and longitudinal images to be generated without requiring the probe body to be physically moved itself. This results in substantially less discomfort for the individual being scanned and treated. The invention is able to capture a significantly greater amount of data, which facilitates the accurate and proper treatment such as brachytherapy, and allows the doctor or technician, or even the treatment planning software or other remote means, significantly greater control of the image plane, which is able to generate a full, volumetric genuine 3-dimensional scan, of the surrounding anatomy, being observed, for any detected disease, and to be treated.

Another object of this invention is to provide a scanning probe that is a rather compact and fully encased mechanism, but yet provides for 3-dimensional scanning and movement of its internal operating components horizontally, transversely, and longitudinally, to furnish a volumetric dimensional actual scan of the body or parts thereof.

Still another object of this invention is to provide a scanning probe that may be inserted, only once, and then rendered fully operative to provide for its precise scanning, without further inconvenience or pain to the patient.

Still another benefit of this invention is the use of miniaturized motors, and other components, encased within a scanning probe, and which furnish all of the movements required to provide a 3-dimensional scan of the surrounding anatomy.

Still a further object of this invention is to provide a volumetric 3-dimensional scanning probe that may be used in conjunction with medical treatment instrumentation, so as to allow the physician to be extremely precise and accurate in the treatment of the patient, such as when, for example, radioisotopes are added to the prostate, or contiguous anatomy, for the treatment of cancer, or the like.

Still another object of this invention is to provide a scanning probe that facilitates the image plane movements normally obtained by a standard probe while used in a stepping device.

A further object of this invention is to provide a scanning probe that may scan various portions of the body A further object of this invention is to provide a body scanning device which substantially lessens the vibrations generated through the use of previous type scanning mechanisms, and which can hinder ultrasonic imaging and cause patient discomfort.

Yet another object of this invention is to provide a form of pulley/sled design for a probe and which provides for a scanning mechanism which can operate in a fluid filled probe tip without changing the volume of the fluid filled tip cavity, negating the need for a fluid filled tip volume compensation means.

These and other objects may become more apparent to those skilled the art upon review of the invention as provided herein, and upon undertaking a study of the description of its preferred embodiment, in light of the drawings.

BRIEF DESCRIPTION OF THE DRAWINGS

In referring to the drawings, FIG. 1 is a perspective view of an ultrasonic probe assembly of the present invention;

FIG. 2 is a cutaway view of the ultrasonic probe assembly shown in FIG. 1, to disclose its internal operative components;

FIG. 3 provides an enlarged and cutaway view of the middle and back sections of the ultrasonic probe, disclosing the various motors, gears, and the motion transmitting shafts, that provide for operative movement to the ultrasonic transducer;

FIG. 4 provides a side view of the front of the probe, as seen in FIG. 2, disclosing the location of the ultrasound transducer and the operative components that provide for its movement during use;

FIG. 16 is an alternative embodiment of the device configured for exterior body scans;

FIG. 17 provides an enlarged and cutaway view of the middle and back sections of a third embodiment of the ultrasonic probe, wherein the inner and outer shafts are controlled via a single motor;

FIG. 20 is a longitudinal view of the scanning probe showing the coupler rings applied thereto; and FIG. 21 provides a more detailed view of the coupler rings, as mounted to the assembly, and showing their oils that generate the electromagnetic fields for transmission of this signal necessary for electronic processing.

DESCRIPTION OF THE PREFERRED EMBODIMENT

Figure 5:
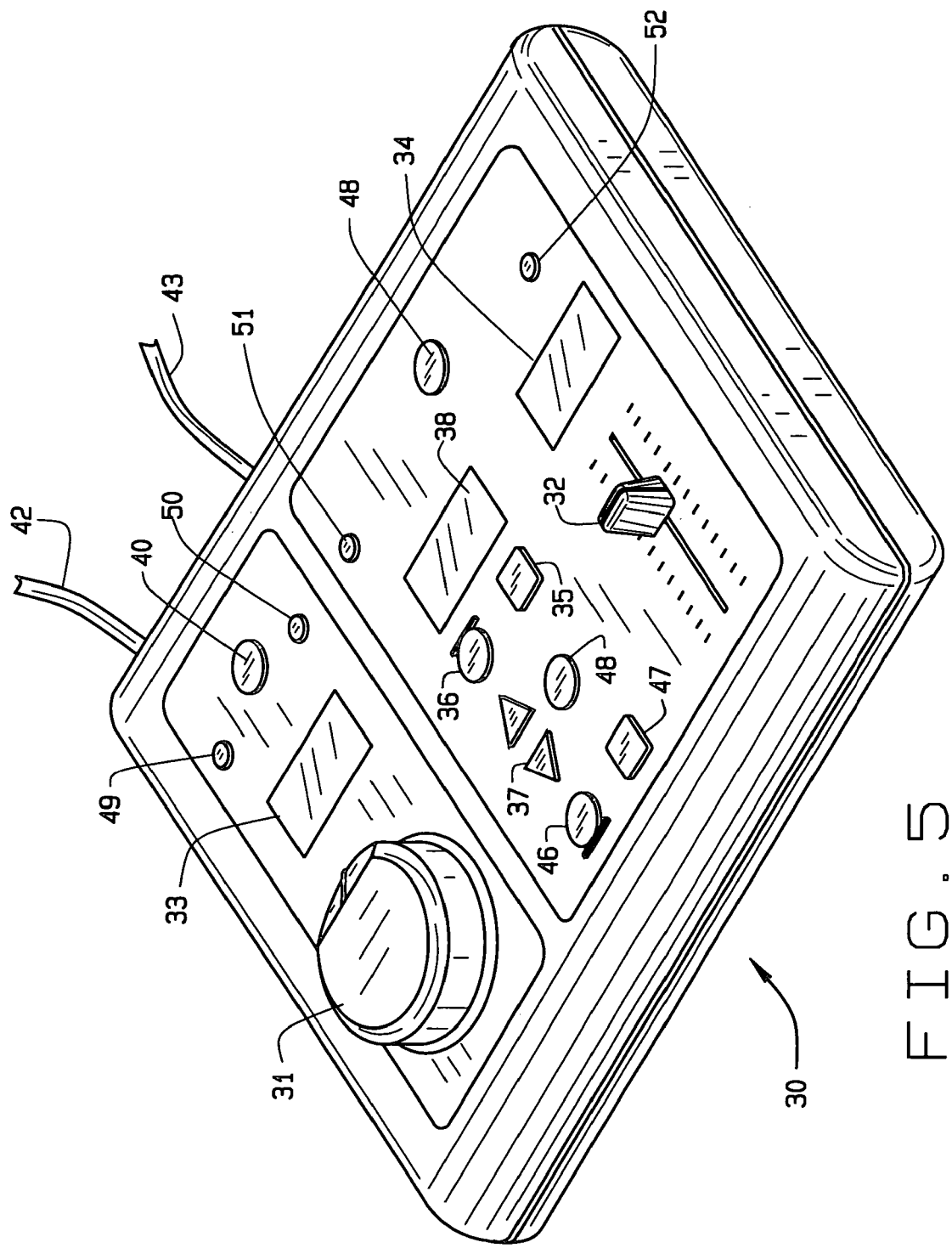
FIG. 5 is an isometric view of an embodiment of the probe control box and its face panel.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 shows the preferred embodiment of a cavital probe 1 of the present invention suitable for transrectal use. The probe 1 is comprised of a handle 1A and tip 1B. Extending from the back of the handle 1A is a probe power and control cable 42. Contained within the handle 1A is a transverse or rotating motor 2 and a longitudinal or linear axis motor 5. The transverse or rotating motor 2 connects to a hollow shaft 13; and the longitudinal motor 5 connects to a shaft 14, which is maintained inside the hollow shaft 13. The shaft 14 may preferably be solid, or of other structure. The hollow shaft 13 is connected to a carriage assembly 3 within the probe tip 1B. The shaft 14 is connected to a vertical bevel gear 6, within probe tip 1B and also within the carriage assembly 3. The carriage assembly 3 (best seen in FIGS. 2 and 4) is comprised of a horizontal bevel gear 7, a lower belt pulley 8, an upper belt pulley 9, a belt 10, an ultrasound transducer 11, an integral belt pin 12, a transducer slide 15 (FIG. 4) and horizontal slider rods 16A and 16B (FIG. 2). The horizontal bevel gear 7 engages with the vertical bevel gear 6, and is fixed to the lower belt pulley 8. The belt 10 is maintained between the lower belt pulley 8 and the upper belt pulley 9. The integral belt pin 12 is positioned in a slot (not shown) on the underside of transducer slide 15. Affixed to the top of the transducer slide 15 is the ultrasound transducer 11. The transducer slide 15 is maintained on the horizontal slider rods 16A and 16B and is configured to slide along the slider rods 16A and 16B. Hence, as can be appreciated, as the belt 10 moves, the transducer slide 15, and consequently, the transducer 14, will move longitudinally through the probe tip 1A (or carriage assembly 3).

Figure 6:
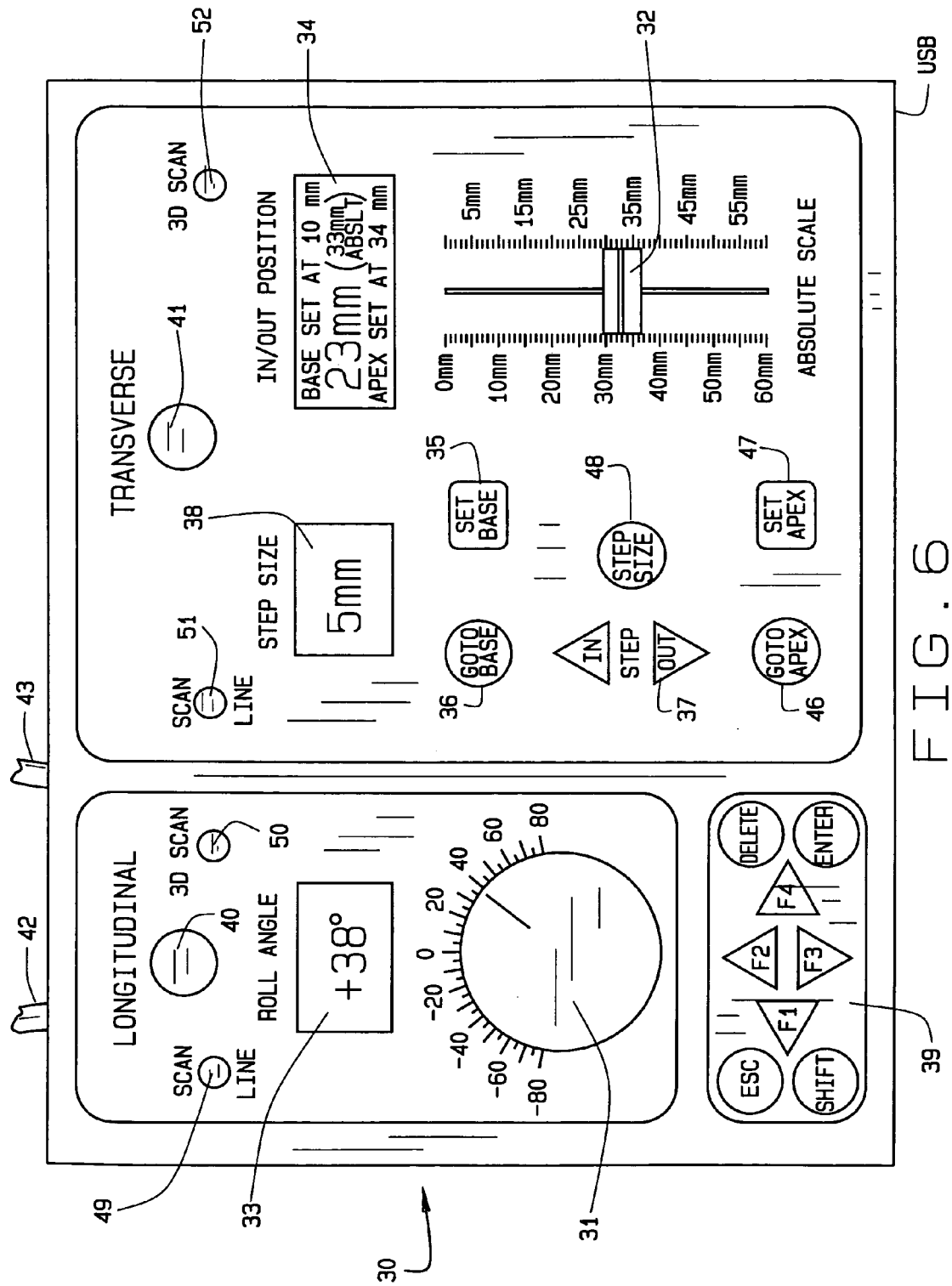
FIG. 6 is a plan view of a control box panel for controlling the probe.
Figure 7:
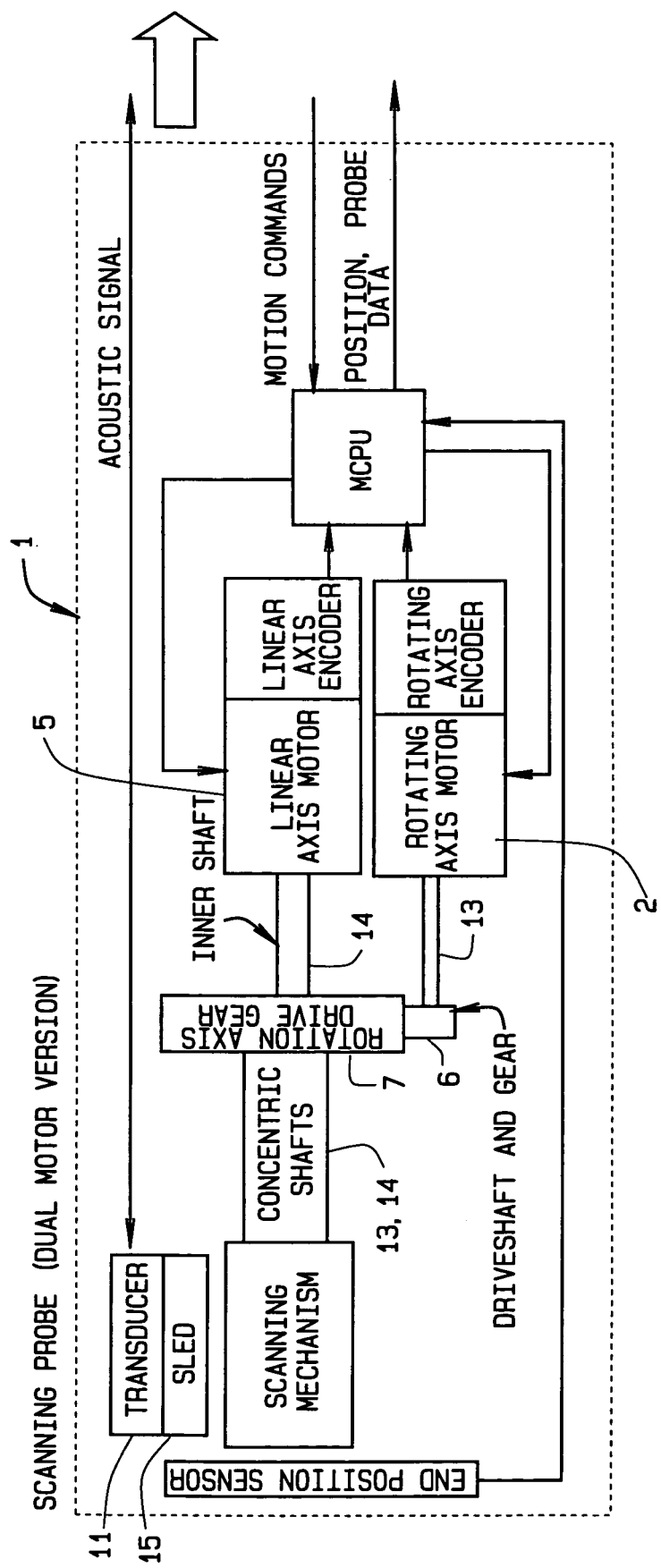
FIG. 7 is a block diagram of the dual motor scanning probe of FIGS. 1–4.

FIGS. 5 and 6 show a preferred embodiment of a control box 30 for the probe 1. The control box 30 includes a variety of displays and control means. Extending from the control box 30 are the probe power and control cable 42 which connects to probe 1 as shown in FIG. 1, and a control box USB connection cable 43. In the alternative, the probe power and control cable could connect to the ultrasound box, as in FIG. 19, as opposed to the control box, as detailed herein. It should be noted that other commercial protocols such as RS-232 or Firewire may be used in place of the USB wire. Although not shown, the control box also includes a power cord to connect the control box to a source of electricity. Although depending on the particular choice of interface, control cable 43 could supply power. Generally configured on the control box 30 are longitudinal control and display means, transverse control and display means and general system control inputs 39. Longitudinal control and display means include roll angle control knob 31, roll angle position indicator 33, longitudinal action initiator 40, longitudinal scan line button 49 and longitudinal 3D scan button 50. The transverse control and display means includes an In/Out position control slider 32, an In/Out position indicator 34, a base placement setting control 35, a "return to base" placement initiator 36, a step size control means 37, a step size control indicator 38, a transverse action initiator 41, a "go to apex" button 46, a "set apex" button 47, a step size button 48, a transverse scan line button 51 and a transverse 3D scan button 52. Contained within the box are electronics necessary for the activation of the device and its control.

Figure 8:
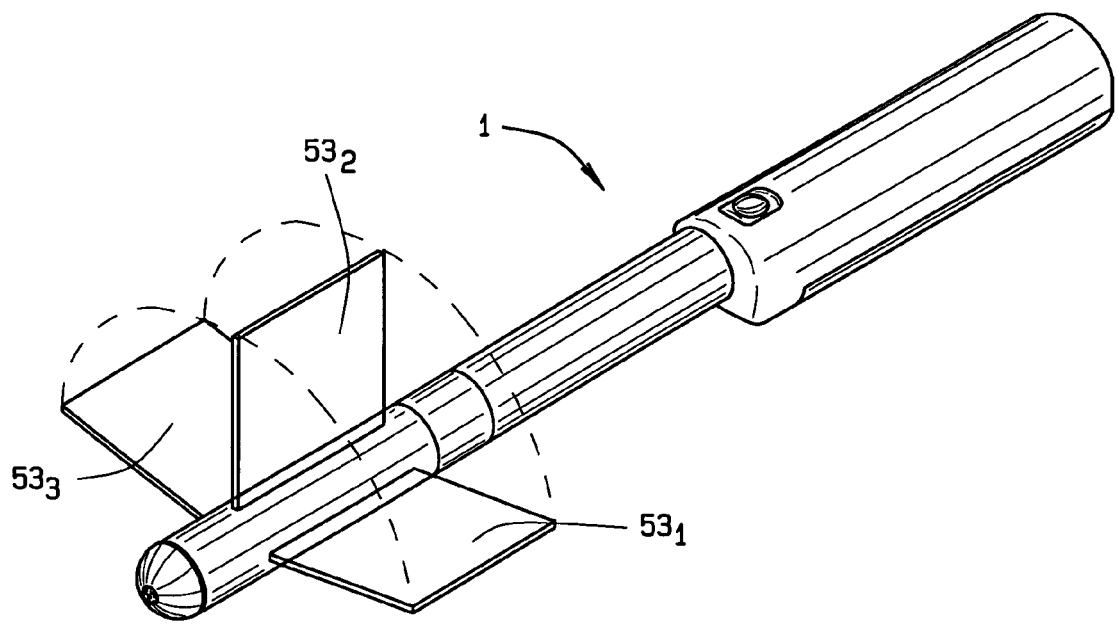
FIG. 8 is a schematic view showing the longitudinal scan planes and their rotational movements for the ultrasonic probe.

FIG. 8 shows longitudinal scan planes $53_1$, $53_2$ and $53_3$.

Figure 9:
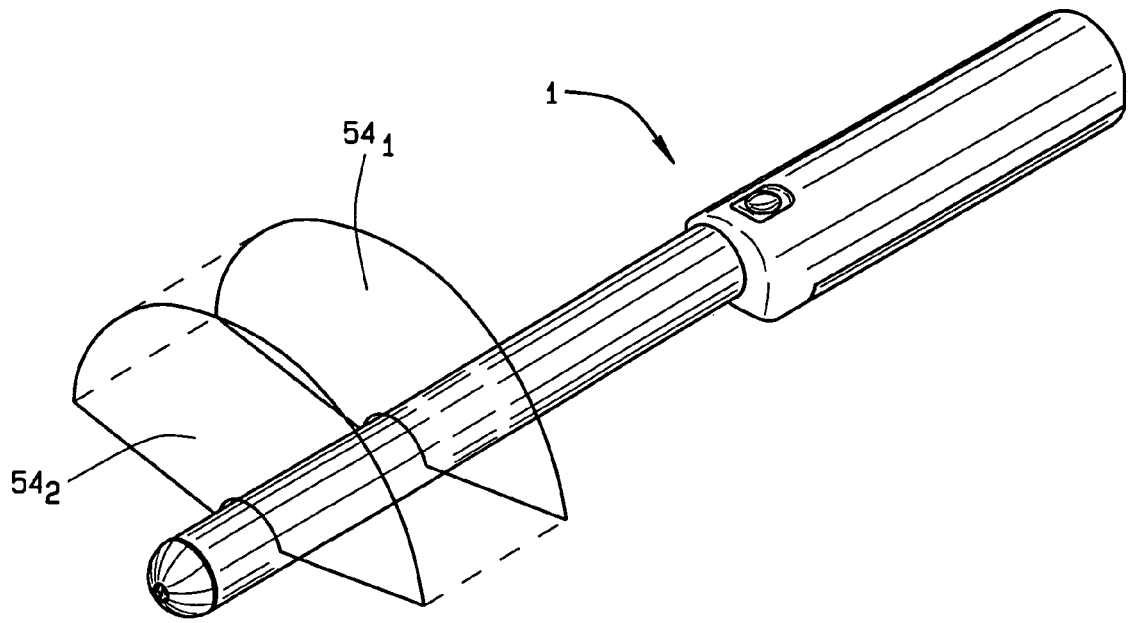
FIG. 9 is a schematic view showing the transverse scan planes and their longitudinal movements for the ultrasonic probe.
Figure 11:
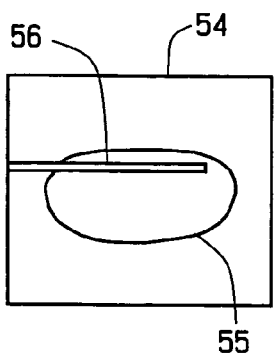
FIG. 11 shows the longitudinal image plane and the locating of the treating needle during its application.

FIG. 9 shows transverse scan planes $54_1$ and $54_2$.

In operation, the control box USB connection is connected to an ultrasonic system with appropriate imaging software. This may include a proprietary system or a computer based imaging system. The probe 1 is inserted transrectally into a patient. The doctor utilizing the probe 1 then selects either longitudinal or transverse imaging, using either the longitudinal action initiator 40 or the transverse action initiator 41, respectively. When longitudinal imaging is selected, the longitudinal motor 5 turns, causing the shaft 14 and vertical bevel gear 6 to turn. The vertical bevel gear 6 is rotationally engaged with the horizontal bevel gear 7, and causes the horizontal bevel gear 7 to rotate. The lower belt pulley 8, is affixed to horizontal bevel gear 7 and is rotated when the bevel gear 7 rotates, causing the upper pulley 9 to rotate and belt 10 to begin moving. As belt 10 moves, integral belt pin 12 also moves, generally being pulled around the pulleys. The integral belt pin 12 is inserted into a slot at the bottom of transducer slide 15, and causes transducer slide 15 to slide back and forth on horizontal slider rods 16A and 16B in a reciprocating motion. As transducer slide 15 moves back and forth, ultrasound transducer 11 is generating pings and then receiving back the selected sound pulse to generate an ultrasound image. As best seen in FIG. 8, the movement of the transducer while generating and receiving signals results in longitudinal scan plane 532.

The doctor may choose to manipulate roll angle control knob 31, which causes the image plane being captured by the ultrasound transducer to rotate relative to the axis of the probe tip 1B, resulting in longitudinal scan planes $53_1$, and $53_3$. Roll angle position indicator 33 indicates the orientation of the image plane, with vertical being zero degrees. Roll angle control knob 31 could incorporate a built-in-position motor so its position will always be automatically updated to be the same as the current longitudinal view angle even if this view angle is changed remotely, such as by the ultrasound system or an optional procedure planning system or other remote means. Roll angle control knob 31 may also incorporate a physical detent or other indexing means, such as a sound indicator, that will allow the doctor to easily reposition and Roll angle control knob 31 and therefore the longitudinal view to the 0 degree straight up position.

Figure 12:
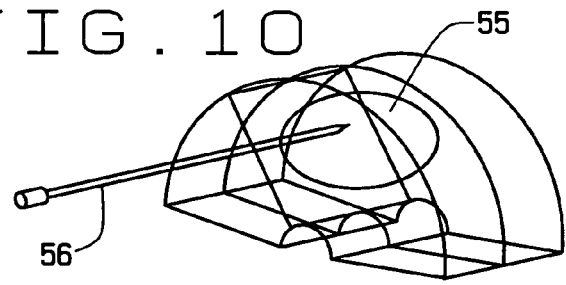
FIG. 12 discloses a volumetric view of the scanned organ with the needle being located therein.

In use, the device may also be utilized to capture a true-solid 3D image data set, by taking a series of adjacent or overlapping longitudinal image slices and recording them into system memory. When a doctor presses the longitudinal 3D scan button 50 the control box 30 initiates a sequence whereby the device images in the longitudinal mode and during or between each longitudinal frame, the transducer rotates perpendicular to the probe shaft until the complete 3D volume is recorded, as best seen in FIG. 12. It is also conceivable that parallel and "slightly skewed" 3D image capture could also be recorded.

Figure 10:
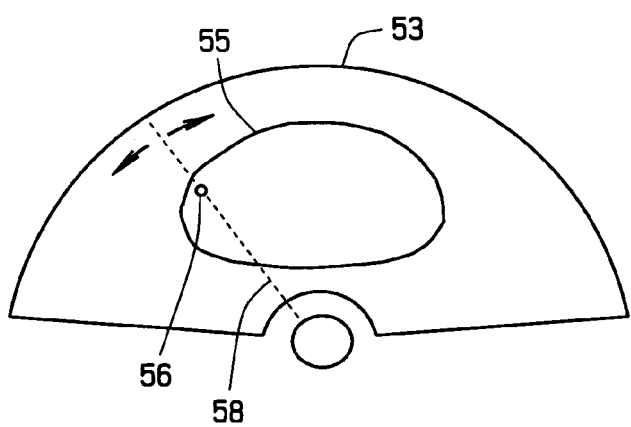
FIG. 10 shows a transverse image plane, in this instance also disclosing the prostate of a patient and the needle during treatment.

Further, in conjunction with imaging software, longitudinal scan line button 49 can be used to display a scan line on an ultrasound display visually indicating the position of the longitudinal scanning plane setting in reference to an image. As seen in FIG. 10, the doctor views the prostate 55 in the transverse view mode by pressing the transverse action initiator 41, resulting in transverse scan plane 53. When a specific area of interest, such as the brachytherapy needle 56 is observed, the physician presses longitudinal scan line button 51. Longitudinal scan line button 51 causes the ultrasound system to display a longitudinal scan line 58 across the displayed transverse scan plane 53 at an angle that corresponds to the angular position of the roll angle control knob 31. Roll angle control knob 31 is then automatically or manually rotated so that the longitudinal scan line 58 intersects the area of interest, in this case brachytherapy needle 56. Next, the physician presses the longitudinal action indicator 40 and brachytherapy needle 56 (or any other area of interest) will automatically show up precisely intersected in the longitudinal view.

When transverse imaging has been selected, the transverse motor 2 is activated causing hollow shaft 13 and inner shaft 14 to turn. The rotation of hollow shaft 13 causes carriage assembly 3 to rotate rapidly around the axis of probe tip 1B. As carriage assembly 3 rotates, ultrasound transducer 11 is generating pings and then receiving back the selected tone to capture an ultrasound image. As best seen in FIG. 9, the movement of the transducer while generating and receiving signals results in transverse scan plane $54_1$.

The doctor may choose to manipulate the In/Out position slider 32, which causes the transverse image plane being captured by ultrasound transducer to move further or closer to the distal end of probe tip 1B, resulting in transverse scan plane $54_2$. The In/Out position indicator 34 indicates the position of the image plane relative to the base (farthest point) or apex (nearest point) of the organ being scanned as well as the absolute position of the transducer relative to the tip of the probe. The In/Out position slider 32 may also incorporate a built-in position motor so its position will always be the same as the current transverse view position even if this view angle is changed remotely such as by the ultrasound system or an optional procedure planning system or another remote means.

Step size control 37 allows the doctor to control the transverse movement in such a manner as to move in pre-determined step increments. Step size increment control indicator 38 displays the selected increment. "Set apex" button 47 allows a doctor to use transverse positioning means to identify the apex, or nearest point, of a scanned organ. Pressing "set apex" button 47 causes the position to be saved in the internal memory of control box and/or ultrasound box 30, and/or in the ultrasound box and/or the computer system. The doctor can then press the "go to apex" button 46 and the device will automatically reposition the ultrasound traducer 11 at the predetermined location. The "set base" button 35 allows a doctor to use transverse positioning means to identify the base, or farthest point, of a scanned organ. Pressing the "set base" button 35 causes the position to be saved in the internal memory of control box 30 and/or ultrasound box, or in the computer system. The doctor can then press the "go to base" button 36 and the device will automatically reposition the ultrasound transducer 11 at the predetermined location.

Figure 15:
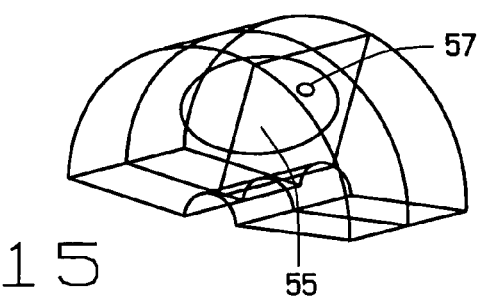
FIG. 15 provides another volumetric scan view of the prostate of the patient.

In use, the device may also be utilized to capture a true-solid 3D image data set, by taking a series of adjacent or overlapping transverse image slices and recording them into system memory. When a doctor presses the transverse 3D scan button 52, the control box 30 initiates a sequence whereby the device images in the transverse mode but during or between each transverse frame, the transducer moves anywhere from a fraction of a millimeter or greater to the distal end of probe tip 1B perpendicular to the probe shaft until the complete 3D volume is recorded, as best seen in FIG. 15. Obviously, parallel or "slightly skewed" 3D image capture can also be recorded.

Figure 14:
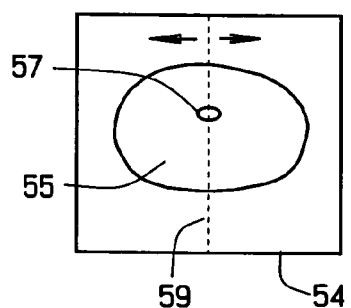
FIG. 14 provides another longitudinal view as observed by the treating physician, of the prostate.
Figure 13:
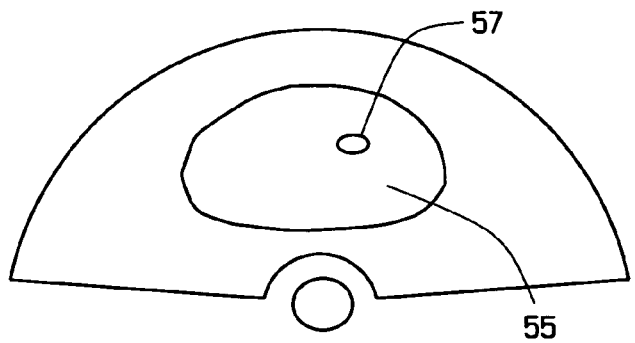
FIG. 13 shows another transverse image plane of the patient being treated.

Further, in conjunction with imaging software, transverse scan line 51 can be used to display a scan line on an ultrasound display visually indicating the position of the scanning plane in reference to an image. As in FIG. 14, the doctor views prostate 55 in the longitudinal view mode by pressing the longitudinal action initiator 40. When a specific area of interest, such as the prostate nodule 57 is observed, the doctor presses transverse scan line button 51. Transverse scan line button 51 will cause the ultrasound system to display a transverse scan line 59 across the longitudinal image plane 54 at a position that corresponds to the In/Out position of the transverse image plane and thus the position of In/Out position slider 32. In/Out position slider 32 is then automatically or manually adjusted so that the transverse scan line 59 intersects the area of interest, in this case prostate nodule 57. Next, the doctor presses transverse action initiator 41 and the prostate nodule 57 (or any other area of interest) will automatically show up precisely intersected in the transverse view. This precise cross sectioning feature will also serve to make positional volume calculations of the prostate, and even much smaller features, very quick and easy.

General system control inputs 39 (FIG. 6) allow control box 30 to interface with software running on the Ultrasound System and/or a Planning Software PC or other remote control means. This will allow the software running on these systems to take advantage of the close proximity of the controls of control box, 30 to the Probe, and could include other control means such as joysticks, track balls, touch pads, etc. In addition, this feature will allow for additional control box features to be added in the future via the specialized software located on either the Ultrasound System and/or a Planning PC System.

Probe 1 and the control box 30 each include a communication interface and protocol that will facilitate the implementation of stand-alone, procedure planning and treatment systems. This interface will allow a planning system to easily control the imaging and positioning movements of probe 1 so that 3D data sets and other procedural images can be acquired.

The ability to move the transducer in and out (longitudinally) within the hollow tip of the probe while also rotating or pivoting, allows the transverse and longitudinal images to also move in and out and to rotate. This allows the probe to generate multiple images without requiring the probe to be physically moved. The ability to maintain the probe in one position while the transducer moves internally has multiple advantages. There is less discomfort for the patient and less chance of moving the prostate and so distorting the image.

A significant advantage of the device is its ability to capture a true-solid 3D image data set. Because the probe remains stationary with only the transducer moving internally, the collection of image data can be much more controlled and precise. Currently image data capture is imprecise and incomplete. The doctor physically moves the probe in and out of the patient in standard increments. While the images are displayed on the ultrasound system as the probe is moved, they are not automatically captured. Instead, the doctor indicates when an image is to be captured, and must also enter in to the system the position of the probe. Typically, a doctor will capture an image slice every five millimeters. These image slices are then used by dosimetry software to electronically recreate the prostate to allow an appropriate volume calculation. The probe 1 is able to capture a true, volumetric 3D data set automatically. Pressing either longitudinal 3D scan button 40 or transverse 3D scan button 52 causes the probe to automatically take a series of overlapping scans of the organ. Because the placement of the transverse is digitally controlled, the system is able to quickly record each of these multiple overlapping scan images in sequence and in position, and then construct a true three dimensional image of the scanned organ. Whereas a conventional probe on a stepper moves in typically five-millimeter increments, the probe 1 is able to take readings at increments of one-millimeter or less instead of just 8 to 10 widely spaced slices.

This solid volume of 3D data can then be viewed and manipulated similarly to that of the 3D data collected by a Clinical Magnetic Resonance Imaging (MRI). Because the transducer movement can be automated, the necessary images can be collected and recorded very quickly to lessen the amount of time the probe must be in the patient's rectum. While an ultrasound exam using a traditional probe can take between 10 to 45 minutes, a full volume scan can be obtained using the probe 1 of the present invention in a much shorter time, with the doctor able to review the images at his or her leisure after the probe is removed. Further, because it is not necessary to insert and remove the probe as part of obtaining image slices, there is no need for the stepper functionality, and the stabilizer can be substantially simpler and less expensive. The control box provides the user with a control interface positioned near the patient.

Further, the device offers substantial advantages when used in conjunction with brachytherapy treatment. This view angle position adjustability will allow the physician to easily find and view needle insertions or the placement of other devices in the longitudinal plane right from the control box. And as mentioned before, not having to physically move the probe and therefore, taking the chance of disturbing the position of the prostate gland, needles, seeds or other devices while acquiring images will in itself help to increase the accuracy of these procedures. In addition, this control has been specifically designed to provide a precise, one-to-one ratio between the control knob angle and the probe roll angle. For example, if the knob is rotated 27 degrees to the left, the probe longitudinal view will also rotate 27 degrees to the left. This one-to-one relationship between the knob angle and the probe roll angle will therefore help the physician to better relate the images they are seeing on the monitor to the spatial environment they are working in. For instance, if they see that they have placed a needle in a grid hole that is approximately 45 degrees to the probe shaft, they then know that they have turned the Angle Control Knob 31 to the same angle to view the needle. A non one-to-one ratio may also be implemented.

This view position adjustability will allow the physician to easily move the view plane form either side of the prostate base and apex, much like a stepping device does, but without having to physically move the probe. And as mentioned before, not having to physically move the probe and therefore, taking the chance of disturbing the position of prostate gland, needles, seeds or other devices while acquiring images, will in itself help to increase the accuracy of these procedures.

And like the longitudinal angle control, this transverse control has been specifically designed to provide a precise, one-to-one ratio between the slider position and the transverse view position, although a non one-to-one ratio may be used. For example, the physician can insert a needle through the needle grid and view the needle tip with the transverse view positioned at the base of the prostate. Next the physician would slide the transverse view slider forward the same distance (for example, 35 mm) that the physician wants to fully insert the needle. Now the physician can insert the needle the exact same distance that he/she just moved the slider and watch as the needle re-appears in the transverse view. This is just another example of how this one-to-one relationship is between the slider position and the transverse view position will help the physician to better relate the images they are seeing to the spatial environment they are working in.

The ability to not have to move the probe manually means that, unlike the existing probe and stepper combinations, the entire probe and probe mount can be covered with a sterile drape because there will be no need to facilitate any type of on (or near) probe controls. This drape will therefore cover this normally cluttered and hard to sterilize area, allowing it to be kept clear for the needle (or any other sterile device) implementation. The control box can also be covered with a form fitting, sterile cover that will allow easy viewing and manipulation of the controls without compromising the sterility of the operator. This will allow the physician to manipulate and hold needles (or any other sterile device) in one hand while controlling the selected probe view with the other hand. The control box will come with a small lightweight floor stand so it can easily be positioned near the probe. After use, the sterile control box covers are simply slipped off of the box and discarded. This will greatly lessen (if not completely alleviate) the need to clean and disinfecting/sterilizing the control box and alleviate any concerns therein.

A second embodiment of the probe is shown in FIG. 16 for external use. The probe 201 includes a casing 203 having a closed top and a closed bottom. The casing 203 encloses motors (not shown). At its imaging end, the scanner 201 includes a pair of slide rods 216. A slide 215 is mounted on the slide rods to be moveable across the opening at the bottom of the probe. A transducer 211 is mounted on the slide 215. The slide 215 and slide rods 216 are positioned below a pulley belt 210. The pulley belt 210 is mounted about a pair of pulleys, one of which is operatively connected to an output shaft of the motor. Hence, when operated, the motor will cause the pulley belt 210 to travel about the pulleys 208 and 209. A pin 212 is operatively connected to the pulley belt 210 and is received in a slot in the bottom of the slide 215. Hence, as the belt 210 travels about the pulleys 208 and 209, the pin 212 will pull the slide 216, and hence the transducer 215 along its path of travel. The pin 212 passes around the pulleys 208 and 209, and hence, has an essentially oval path of travel. As the pin moves in its oval path, it moves the transducer 211 back and forth across the imaging end in a reciprocal fashion. Further, the entire carriage can rotate, providing the transverse view similar to the preferred embodiment.

Figure 18:
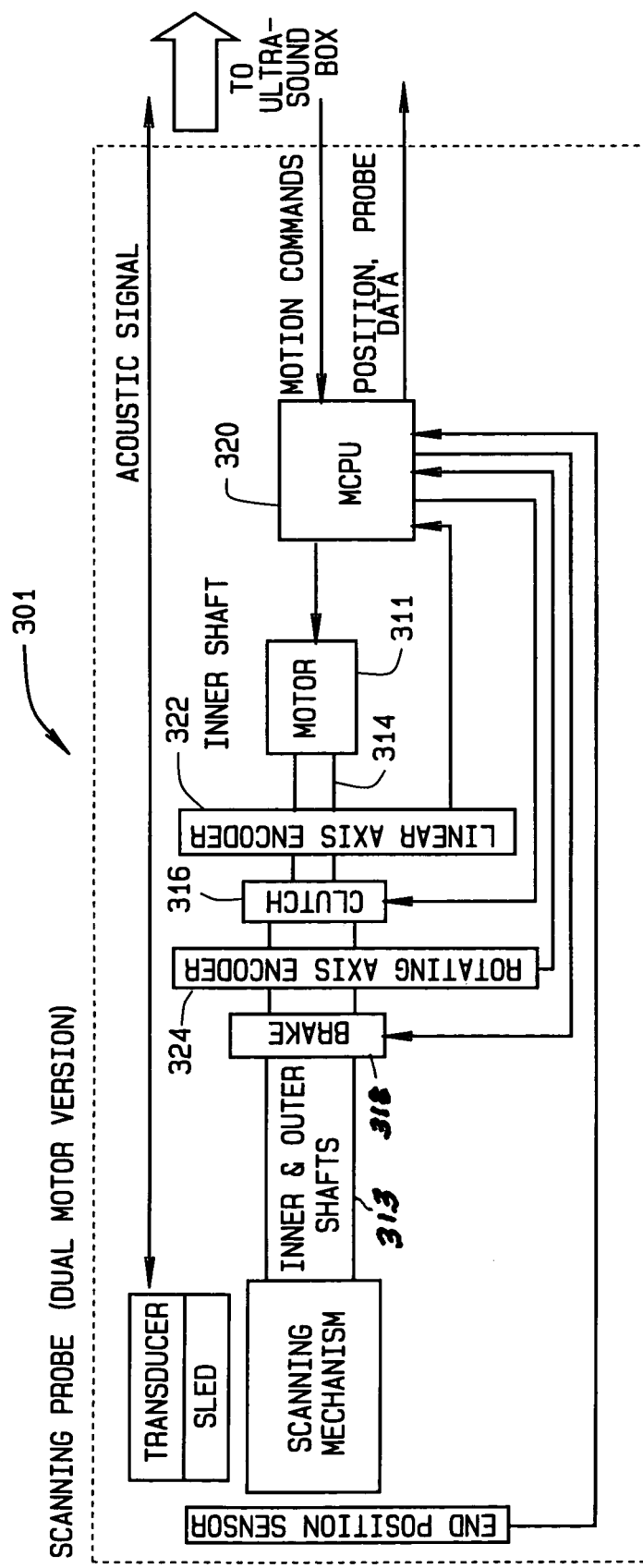
FIG. 18 is a block diagram of the single motor scanning probe of FIG. 17.

A third embodiment of the probe is shown in FIG. 17, and in block diagram format if FIG. 18. The probe 301 is similar to the probe 1 and includes a handle 301A and a tip 301B. The tip 301B is substantially similar to the tip 1B of the probe 1, and will not be described further. Unlike the probe 1, the probe 301 includes a single motor 311. An inner shaft 314 is rotatably driven by the motor 311. As in the probe 1, the shaft 314 extends through to the probe tip 301B to linearly and reciprocally drive the sled and transducer. A clutch 316 is mounted about the inner shaft 314, and the outer shaft 313 extends from the clutch 316. The outer shaft 313 is hollow, and the inner shaft 314 extends through the outer shaft 313. When the clutch 316 is engaged, the clutch locks the inner and outer shafts together, such that the outer shaft will be rotated by the rotation of the inner shaft. The outer shaft, in turn, is connected to the tip 301B to rotate the scanning mechanism (which contains the sled, slide rods, transducer, pulleys, and pulley belt), as described above with the probe 1. An outer shaft brake 318 is mounted about the outer shaft 313 forwardly of the clutch 316. The brake 318 is operable to prevent rotation of the outer shaft. Although, the entire carriage may rotate through the energization of one of the motors.

The clutch 316 and brake 318 are controlled by a motion control processing unit (MCPU) 320. The MCPU is operatively connected to the control box 30. In response to operation command signals received from the control box 30, the MCPU engages and disengages the clutch and brake to allow for rotational and reciprocal motion of the transducer in the probe tip 301B. Thus, to move the transducer linearly along the axis of the probe tip, the clutch is released and the brake is applied. Conversely, to rotate the transducer about the axis of the probe tip, the clutch is engaged, and the brake is released. Upon release of the brake 318, the outer shaft can move to rotate the scanning mechanism. Hence, when the physician activates the probe 301 using the control box 30, as described above, MCPU will signal the clutch and brake to move the transducer rotationally and/or longitudinally, depending on the commands initiated by the physician.

To monitor the longitudinally and rotational position of the transducer, the probe includes a linear axis encoder 322 and a rotating axis encoder 324. The encoders each include a wheel which rotates with the respective shaft, and a sensor which monitors the rotational position of the wheel. Such encoding assemblies are well known in the art. The encodes 322 and 324 send signals to the MCPU indicative of the longitudinally and rotational position of the transducer. This information is then displayed on the control unit 30, as described above.

Figure 19:
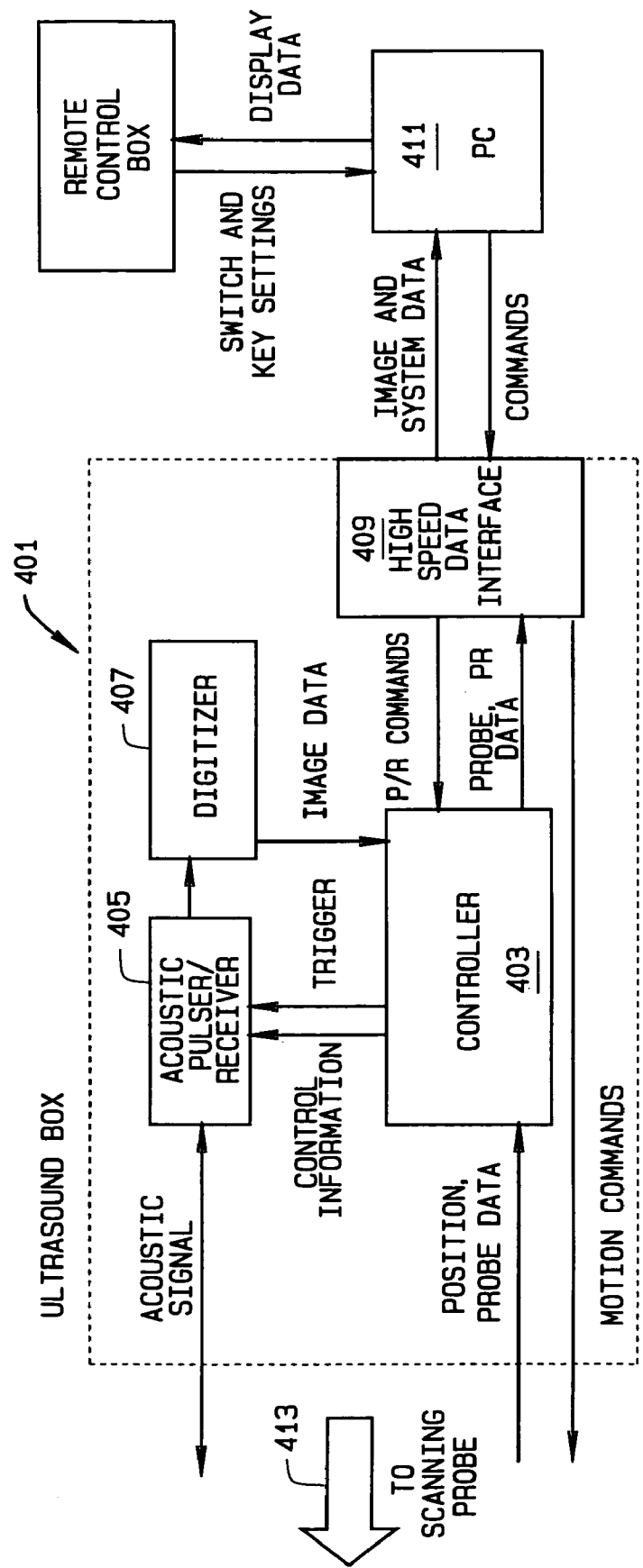
FIG. 19 is a block diagram of the ultrasound box used with the scanning probes.

A block diagram of an ultrasound box 401 is shown in FIG. 19. The ultrasound box is used to control the probes 1, 201, and 301. The ultrasound box 401 includes a controller 403, a pulser/receiver 405, a digitizer 407, and a high speed data interface 409. The ultrasound box 401 receives commands from an external computer or PC 411 via the data interface 409. These commands are used to configure both the pulser/receiver 405 and the probe. An acoustic pulse is generated in the pulser/receiver 405 sent to the scanning probe over a coaxial cable 413. Backscattered ultrasound data is returned to the ultrasound box 401 from the probe transducer and is processed by the receiver 405. The data is then digitized by the digitizer 407 and sent to a memory buffer in the controller 403. The data is then sent to the PC 411 for image formation and display via the data interface 409.

As can be seen in FIG. 20, affixed to one end of the carriage assembly 3 is a magnetic coupler ring 500, such that the coupler ring 500a rotates with the carriage assembly, as with its shaft 501. Attached to the back side of the coupler ring 500a is the connecting wire 502 that electrically connects to the transducer 503. Cooperatively associated with the coupler ring 500a is the coupler ring 500b, which is affixed to the probe back 504. Connecting to the coupler ring 500b is the connecting wire 505, which is in turn electrically connected to the pulsar receiver 505, assembled with the ultrasound power and control means. See FIG. 19. As electricity is transmitted to the transducer 3, a magnetic field is generated by the coil inherent in the first magnetic coupler ring 500b. This field traverses the air gap, as at 506, between the coupler ring 500b and the coupler ring 500a, and generates a similar magnetic field in the inherent coils of both magnetic coupler rings, which is also translated into a signal. Thus, the magnetic coils actually operate similar to that as brushes in an electric motor. Conversely, as a signal is received back from a pulse by the transducer 503, that signal transverses the gap between the coupler rings, and transmits the signal back to the necessary the necessary ultrasound electronics, for further processing. As can be seen in said FIG. 19, this provides for processing of the signal between the moving and stationary portions of the carriage assembly and the stationary portion of the probe, allowing the signal to be transmitted back to the electronics, for processing.

FIG. 21 discloses a more detailed view of the magnetic couplers as described in FIG. 20.

As various changes could be made in the above constructions without departing from the scope of the invention, it is intended that all matter contained in the above description or shown in the accompanying drawings shall be interpreted as illustrative and not in a limiting sense. For example, the path along which the transducer sled reciprocates could be formed by structure other than the slide rods. For example, the sled could move along the track that is formed in the tip. Additionally, means other than a belt and pulley can be used to reciprocally move the sled (and hence the transducer). These examples are merely illustrative.

What is claimed is:

1. An ultrasonic probe assembly comprising:

a housing having a handle and a tip, said tip having an axis;

said probe including a carriage assembly and a scanning probe;

a scanning assembly contained within said tip; said scanning assembly comprising a track generally parallel to said tip axis, a sled mounted on said track to be moveable along said track; and a transducer mounted on said sled;

a drive operatively connected to said sled to move said sled along said track, and including a magnetic coupler electrically connected between the carriage assembly and the scanning probe for use for transmitting a signal between said carriage assembly and the scanning probe for further processing.

2. The device of claim 1 wherein the magnetic coupler includes a pair of coupler rings, one ring being connected into the carriage assembly for rotation, while the second coupler ring stationarily mounts to the scanning probe.

3. A multi-plane ultrasonic probe assembly for use for ultrasound medical scanning of a part of the body whereby upon locating of the probe within the body it remains stationary while the assembly provides multi-plane scanning, comprising:

a housing having a handle and a probe tip, said probe tip having an axis;

a scanning assembly contained within said probe tip and being rotatable in said probe tip to provide radial scanning of a proximate body part;

said housing including a carriage assembly, and said scanning assembly including a scanning probe;

a transducer operatively associated with said scanning assembly, a drive operatively connected to said scanning assembly to rotate said scanning assembly and to move said transducer longitudinally in said probe tip, to provide multi-plane scanning of a body part without any movement the ultrasonic probe once inserted, and including a magnetic coupler electrically connected between the carriage assembly and the scanning probe for use for transmitting a signal between said carriage assembly and the scanning probe for further processing.

* * * * *